United States Patent [19]

Honeycutt et al.

[11] Patent Number: 5,620,786

[45] Date of Patent: Apr. 15, 1997

[54] HOT WATER SOLUBLE TOWELS, SPONGES AND GAUZES

[75] Inventors: Travis W. Honeycutt, Gainesville; Baosheng Lee, Duluth, both of Ga.

[73] Assignee: Isolyser Co. Inc., Norcross, Ga.

[21] Appl. No.: 286,814

[22] Filed: Aug. 5, 1994

Related U.S. Application Data

[63] Continuation-in-part of Ser. No. 55,083, Apr. 29, 1993, abandoned.

[51] Int. Cl.$^6$ .................................................. D03D 3/00
[52] U.S. Cl. ........................... 442/50; 264/185; 442/327; 442/365
[58] Field of Search ........................... 428/229, 288, 428/85, 224, 255, 225, 253, 257, 299; 264/185

[56] References Cited

U.S. PATENT DOCUMENTS

| | | |
|---|---|---|
| 2,340,866 | 2/1944 | Dangelmajer . |
| 2,395,616 | 2/1946 | Dangelmajer . |
| 2,408,377 | 10/1946 | Dangelmajer . |
| 2,430,949 | 11/1947 | Porter et al. . |
| 2,909,502 | 10/1959 | Matsumoto et al. . |
| 3,089,493 | 5/1963 | Galindo . |
| 3,314,809 | 4/1967 | Klug . |
| 3,372,311 | 3/1968 | Lobur . |
| 3,413,229 | 11/1968 | Bianco et al. . |
| 3,484,874 | 12/1969 | Bickenheuser, Jr. . |
| 3,578,619 | 5/1971 | Reeder . |
| 3,607,812 | 9/1971 | Takigawa et. al. . |
| 3,637,657 | 1/1972 | Morii et al. . |
| 3,762,454 | 10/1973 | Wilkins, Jr. . |
| 3,790,067 | 2/1974 | Scheier . |
| 3,859,125 | 1/1975 | Miller et al. . |
| 3,865,918 | 2/1975 | Mitchell et al. . |
| 3,886,112 | 5/1975 | Watson et al. . |
| 3,886,610 | 6/1975 | Shelden . |
| 3,930,086 | 12/1975 | Harmon ............................ 428/131 |
| 3,931,088 | 1/1976 | Sakurada et al. . |
| 4,073,733 | 2/1978 | Yamauchi et al. . |
| 4,079,036 | 3/1978 | Ohmori et al. . |
| 4,258,849 | 3/1981 | Miller ............................... 206/812 |
| 4,279,752 | 7/1981 | Sueoka et al. . |
| 4,295,850 | 10/1981 | Haberli et al. . |
| 4,343,133 | 8/1982 | Daniels et al. . |
| 4,478,971 | 10/1984 | Ballard . |
| 4,612,157 | 9/1986 | Genba et al. ..................... 264/185 |
| 4,620,999 | 11/1986 | Holmes . |
| 4,651,725 | 3/1987 | Kifune et al. . |
| 4,952,550 | 8/1990 | Wallach et al. . |
| 4,959,341 | 9/1990 | Wallach . |
| 4,959,464 | 9/1990 | Yeh . |
| 4,971,861 | 11/1990 | Watanabe et al. ............... 428/364 |
| 5,051,222 | 9/1991 | Marten et al. . |
| 5,106,890 | 4/1992 | Maruhashi et al. . |
| 5,181,966 | 1/1993 | Honeycutt et al. . |
| 5,181,967 | 1/1993 | Honeycutt . |
| 5,183,571 | 2/1993 | Hanel et al. . |
| 5,207,837 | 5/1993 | Honeycutt . |
| 5,208,104 | 5/1993 | Ueda et al. ...................... 428/364 |
| 5,225,120 | 7/1993 | Graiver et al. . |
| 5,268,222 | 12/1993 | Honeycutt ........................ 428/224 |

FOREIGN PATENT DOCUMENTS

| | | |
|---|---|---|
| 8902229 | of 0000 | Brazil . |
| 0107576A2 | of 0000 | European Pat. Off. . |
| 0176316A2 | of 0000 | European Pat. Off. . |
| 0050288A1 | of 0000 | European Pat. Off. . |
| 3017246A1 | of 0000 | Germany . |
| 1519530 | of 0000 | Germany . |
| 2-68396 | of 0000 | Japan . |
| 63-200764 | of 0000 | Japan . |
| 55-71532 | of 0000 | Japan . |
| 47-41741 | of 0000 | Japan . |
| 61-159995 | of 0000 | Japan . |
| 59-100704 | of 0000 | Japan . |
| 60-44897 | of 0000 | Japan . |
| 5-321105 | 12/1993 | Japan ............................... D04H 1/12 |
| 2248842 | of 0000 | United Kingdom . |
| 2227245 | of 0000 | United Kingdom . |
| 2211196 | of 0000 | United Kingdom . |
| 2211088 | of 0000 | United Kingdom . |
| 2119709 | of 0000 | United Kingdom . |
| 2102461 | of 0000 | United Kingdom . |
| 20837628 | of 0000 | United Kingdom . |
| 1451619 | of 0000 | United Kingdom . |
| 1374199 | of 0000 | United Kingdom . |
| 1312370 | of 0000 | United Kingdom . |
| 1271424 | of 0000 | United Kingdom . |
| 1187690 | of 0000 | United Kingdom . |
| 743165 | of 0000 | United Kingdom . |
| 386161 | of 0000 | United Kingdom . |
| WO91/17210 | of 0000 | WIPO . |
| WO80/01374 | of 0000 | WIPO . |

*Primary Examiner*—James J. Bell
*Attorney, Agent, or Firm*—Malcolm B. Wittenberg

[57] ABSTRACT

Towel, sponge and gauze products composed of fibers of polyvinyl alcohol resin. The fibers are selectively soluble in aqueous solutions only above approximately 93° C. Polyvinyl alcohol fibers have a degree of hydrolysis of at least 99%, are composed of no more than ½% sodium acetate, ¹⁄₁₀% methyl alcohol and an average degree of polymerization between approximately 1300 to 1500. The polyvinyl alcohol fibers being produced by a process of dope extrusion.

30 Claims, No Drawings

HOT WATER SOLUBLE TOWELS, SPONGES AND GAUZES

CROSS-REFERENCE TO RELATED APPLICATIONS

This application is a continuation-in-part of application Ser. No. 08/055,083, filed Apr. 29, 1993 now abandoned.

FIELD OF THE INVENTION

The present invention deals with specific products, namely, towels, sponges and gauzes which are produced from selectively hot water soluble polyvinyl alcohol resins, The resins are configured into fibers which are, in turn, used to construct the subject finished product.

BACKGROUND OF THE INVENTION

Hospital patient care generates considerable quantities of infectious medical waste in primary and acute care facilities. There has been a general conversion from reusable, cleanable items, to disposable items over the last three decades. These conversions were made to promote antiseptic techniques in patient care and to decrease the potential for cross-infections between patients, staff and the general public. Recent federal and state government regulations such as the Medical Waste Tracking Act of 1988 and OSHA Medical Facility rules have resulted in a substantial increase in medical waste that must be classified as "infectious."

When a patient is admitted to a hospital, the patient produces approximately 55 pounds of medical waste per day. Approximately 20% of this waste is infectious. The current stated objective of the American Hospital Association and the Centers for Disease Control is to treat medical waste as soon as it is generated. Both organizations recognize that medical waste is primarily an occupational hazard for health care workers and not an environmental problem. The best way to deal with infectious medical waste is to disinfect it at the point of generation and dispose of the treated medical waste with minimum handling and storage on premises.

The need for an effective way to dispose of medical waste has been highlighted by the amendment made to 29 C.F.R. §1910.1030 which provides for the federal regulation under the Occupational Safety And Health Act, 29 U.S.C. 655,657 to control bloodborne pathogens. Specifically, the Act calls for the establishment of an exposure control plan, the containment of specimens of blood or other potentially infectious materials and the general tightening of precautionary measures to minimize the spread of disease. A safe and effective way to dispose of hospital waste would greatly facilitate compliance with the above-referenced Act.

As a result, consumption of medical disposable woven or non-woven products has been growing at a rate of approximately 10% a year. In 1988, sales totaled approximately 1.155 Billion Dollars. It is projected that by 1994, sales of medical disposable woven and non-woven products will reach 2.05 Billion Dollars.

In the United States, there are approximately 30 million surgical procedures performed each year. After each surgical procedure, it is necessary that the operating theater be disinfected and sterilized before a new procedure is performed to minimize any exposure the patients may bring to other patients or staff. This is particularly important in light of today's increasingly stringent regulations regarding occupational exposure to blood and bodily fluids.

Towels, sponges and gauzes have been in use since the first days of surgical procedures. They are used either to manipulate tissue, absorb blood and other oxidants of the wound site, as well as being useful to cleanse hands and assist in cleansing certain utensils used in various surgical procedures. Traditionally, towels, sponges and gauzes have been made from cotton fibers, though in recent years attempts have been made to provide replacements from other fibers including polyesters, rayons and other staple materials. These fibers were chosen because of their relative availability and cleanliness as man-made materials. Cotton is an agricultural material with volatile price and availability fluctuations. It has been noted that cotton replacements have, by and large, been unsatisfactory although many attempts have been made to mimic the appearance of cotton, all of which have been in vain.

Hospitals generally discard gauzes, sponges and towels after surgical use. Disposal takes place in either a landfill or by incineration. However, in either case, the handling of articles after use promotes the exposure of certain blood borne diseases to those employees who are charged with the responsibility for bagging and introducing such materials into the disposal process.

It is thus an object of the present invention to provide suitable towels, sponges and gauze capable of being disposed of after use while avoiding additional burdens being placed upon landfills and other disposal sites.

It is yet a further object of the present invention to provide suitable towels, sponges and gauze which, after use, can be solubilized and substantially sterilized in a single operation.

These and further objects will be more readily appreciated when considering the following disclosure and dependent claims.

SUMMARY OF THE INVENTION

The present invention involves an article comprising a member selected from the group consisting essentially of towels, sponges and gauzes. The article is comprised of fibers of polyvinyl alcohol resin which are selectively soluble in aqueous solutions only above approximately 93° C. The polyvinyl alcohol fibers are characterized as having a degree of hydrolysis of at least 99%, being composed of no more than ½% sodium acetate and ¹/₁₀% methyl alcohol and an average degree of polymerization between approximately 1300 to 1500. The polyvinyl alcohol fibers are produced by a process of dope extrusion and then treated with heat and stretching, the degree of crystallinity and the degree of orientation for the heated and stretched polyvinyl alcohol fibers are approximately 0.70 and 0.52 respectively.

The degree of crystallinity and the degree of orientation is measured by IR spectroscopy. Degree of crystallinity is the ratio of crystalline area to amorphous area. Degree of orientation is the ratio of non-oriented area to oriented area.

DETAILED DESCRIPTION OF THE INVENTION

As noted, the present invention deals with novel towels, sponges and gauzes and a method of disposal for use primarily in the medical industry in hospitals, outpatient facilities, and home environments. At such facilities, towels, sponges and gauzes, particularly in surgical theaters, generally come into contact with human bodily fluids such that disposal and disinfection has become a matter of major concern in light of the lack of biodegradability of prior products and the potential spread of human-borne diseases such as hepatitis-B and AIDS.

In order to cope with these difficulties, it is proposed that suitable towels, sponges and gauzes be composed of fabric produced from fibers comprising polyvinyl alcohol which is water soluble at temperatures only above approximately 93° C. If such articles were soluble at lower temperatures, inadvertent solubilization would occur in the event that the towels, sponges or gauzes were to contact certain fluids above room temperature such as human bodily fluids generated during ordinary surgical procedures. Working with polyvinyl alcohol which dissolves only at higher temperatures such as above approximately 93° C. would prevent inadvertent solubilization yet remain viable in practicing the present invention. In fact, it is contemplated that disposal in a hot water bath such as a washing machine at or near the boiling point of water dedicated solely to solubilizing such products would be an effective disinfecting media. As such, two objectives could be accomplished, namely, that the polymer would be disinfected and would be solubilized for disposal through the sewer systems. Not only would this lessen the burden now being imposed upon current landfill sites, but liquid sewer disposal would provide a comparatively low cost technique in ridding the user of soiled towels, sponges and gauzes.

In one embodiment, articles produced by practicing the present invention could be formed from a yarn which is a unit made from a multiplicity of fibers. The yarn can be formed as either a staple or as filament fibers made from polyvinyl alcohol. This nontoxic, synthetic polymer is produced by alkali or acidic hydrolysis of polyvinyl acetate. The vinyl acetate monomer is produced by reacting either acetylene and acetic acid or ethylene, acetic acid and oxygen. Polyvinyl alcohol can be manufactured as a water soluble or insoluble resin.

Water soluble resins of polyvinyl alcohol can be hot and cold water soluble or hot water soluble only. The temperature at which polyvinyl alcohol dissolves is controlled by changing its degree of hydrolysis, polymer crystallization and orientation, that is, how the polymers are bound to each other. The polyvinyl alcohol resin used in the present invention is intended to have a general range of hydrolysis of greater than 99%, less than ½% sodium acetate, less than 1/10% methyl alcohol with a degree of polymerization between 1300 and 1500 as an average.

Polyvinyl alcohol fibers used herein are formed by dissolving suitable hot water soluble polyvinyl acetate resin into deionized or distilled water to a 5% to 15% by solids mixture, thereby creating a "dope." This dope is then allowed to stand for a considerable period of time, for example two weeks, for gel setting. All attempts should be made to keep the dope free of microbial organisms as polyvinyl alcohol is subject to microbial degradation when in solution. This can be accomplished either through ultrafiltration, heating or other means well known to those intent on preserving resin solutions. Such techniques include the addition of anti-microbials such as ester phenolic derivatives such as salicylic or benzoic esters.

Once the above-described resin has been gel set, it is then filtered and forced through a spinneret and into a saturated solution of sodium sulphate wherein the fibers are coagulated into a range of deniers of from 6 to 10. The fiber is then subjected to a drawing between a 2:1 and 5:1 ratio, with 4:1 ratio preferred and heat annealed at their glass transition point to produce hot water soluble fibers. The degree of crystallinity and the degree of orientation for the heated and stretched polyvinyl alcohol fibers are approximately 0.70 and 0.52 respectively. The fibers so produced are then either chopped into a staple between approximately 1" to 2" in length or formed into tow bundles which can then be stretch broken with a fiber length of 1" and 6". These fibers are then formed into a yarn either by conventional cotton spinning methods, woolen spinning methods or spun directly from the stretch broken tow. A preferred yarn size is between 60 singles and 0.5 singles, with up to four plies of each of these yarns. The yarns can be spun in the Z or S direction with a weaving twist multiple between 3 and 6 with 3.5 to 4.0 twist multiple preferred.

The above-described yarn can be colored, if desired. If colored, the yarn should be dope dyed in the resin solution. Pigments are useful that are insoluble in water to produce the highest quality light sublimentation and mark-off resistance. Fabric can be formed by weaving or by other well known techniques. For example, yarns can be intermingled in a perpendicular fashion or can be woven, or yarns can be single knit, double knit, interlocked, warped knit, or crocheted, as desired. It is even possible to bypass the yarn formation method and produce a nonwoven fabric directly from the fiber which is commonly referred to as either air laid, dry laid, wet laid, hydroentangled, thermo bonded, or chemical bonded. Uniquely, these products are formed into fabrics, de-sized as necessary and cut, sewn and uniquely washed at up to 160° F. before further processing. These items, while intended to be single use disposable products in hot water, are uniquely exposed to water between 30° and 60° C. to reduce bioburden, remove fugitive color, bleach or wash away stray bits of fiber and yarn which may become contaminants in the wound site.

What is claimed is:

1. An article comprising a member selected from the group consisting essentially of a towel, sponge and gauze, said article being comprised of fibers of polyvinyl alcohol resin which are soluble in aqueous solutions only above approximately 93° C., said polyvinyl alcohol fibers being further characterized as having a degree of hydrolysis of at least approximately 99%, being composed of no more than ½% sodium acetate and 1/10% methyl alcohol and an average degree of polymerization between approximately 1300 to 1500, said polyvinyl alcohol fibers being produced by a process of dope extrusion and then treated with heat and stretching, the degree of crystallinity and the degree of orientation for the heated and stretched polyvinyl alcohol fibers are approximately 0.70 and 0.52 respectively.

2. The article of claim 1 wherein a dope of polyvinyl alcohol is formed by a process which comprises dissolving said polyvinyl alcohol resin in deionized or distilled water at a concentration of from approximately 5 to 15% (wt.).

3. The article of claim 2 wherein a gel of said polyvinyl alcohol dope is formed, said gel being substantially free of microbial organisms which would result in microbial degradation of said gel if present.

4. The article of claim 3 wherein said polyvinyl alcohol fibers are formed by filtering said gel and forcing said filtered gel through a spinneret and into a substantially saturated solution of sodium sulfate.

5. The article of claim 4 wherein said polyvinyl alcohol fibers are coagulated into a range of deniers between approximately 6 to 10.

6. The article of claim 5 wherein said polyvinyl alcohol fibers are subjected to drawing at a ratio between a range of approximately 2:1 to 5:1.

7. The article of claim 5 wherein said polyvinyl alcohol fibers are subjected to drawing at a ratio of approximately 4:1.

8. The article of claim 6 wherein said polyvinyl alcohol fibers are heat annealed at approximately the glass transition temperature thereof in producing polyvinyl alcohol fibers which are soluble only in aqueous solutions above 93° C.

9. The article of claim 1 wherein said fibers of polyvinyl alcohol are chopped into a staple between approximately 1" to 2" in length.

10. The article of claim 1 wherein said fibers of polyvinyl alcohol are produced by forming a tow bundle of polyvinyl alcohol fibers which are stretch broken with average fiber length of between approximately 1" to 6".

11. The article of claim 1 wherein said polyvinyl alcohol fibers are formed into yarns which are then combined to produce said towel, sponge or gauze.

12. The article of claim 11 wherein said yarn is produced from said fibers by a method of cotton spinning.

13. The article of claim 11 wherein said yarn is produced from said fibers by a method of woolen spinning.

14. The article of claim 11 wherein said yarn is produced by spinning directly from broken tow of said polyvinyl alcohol fibers.

15. The article of claim 11 wherein said yarn is sized between approximately 60 singles and 0.5 singles.

16. The article of claim 11 wherein said towel, sponge or gauze comprises up to approximately 4 plies of said yarn.

17. The article of claim 11 wherein said towel, sponge or gauze comprises yarn spun in either the Z or S direction with a weaving twist multiple between 3 and 6.

18. The article of claim 17 wherein said weaving twist multiple is between 3.5 to 4.0.

19. The article of claim 2 wherein a pigment is added to said solution of polyvinyl alcohol resin, said pigment being substantially insoluble in water.

20. The article of claim 11 wherein said yarn is subjected to a single knit process to form said towel, sponge or gauze.

21. The article of claim 11 wherein said yarn is subjected to a double knit process to form said towel, sponge or gauze.

22. The article of claim 11 wherein said yarn is subjected to a interlock knit process to form said towel, sponge or gauze.

23. The article of claim 11 wherein said yarn is subjected to a warped knit process to form said towel, sponge or gauze.

24. The article of claim 11 wherein said yarn is subjected to a crocheted knit process to form said towel, sponge or gauze.

25. The article of claim 1 wherein said towel, sponge or gauze is produced from a nonwoven fabric of air laid polyvinyl alcohol fiber.

26. The article of claim 1 wherein said towel, sponge or gauze is produced from a nonwoven fabric of dry laid polyvinyl alcohol fiber.

27. The article of claim 1 wherein said towel, sponge or gauze is produced from a nonwoven fabric of wet laid polyvinyl alcohol fiber.

28. The article of claim 1 wherein said towel, sponge or gauze is produced from a nonwoven fabric of hydroentangled polyvinyl alcohol fiber.

29. The article of claim 1 wherein said towel, sponge or gauze is produced from a nonwoven fabric of thermo bonded polyvinyl alcohol fiber.

30. The article of claim 1 wherein said towel, sponge or gauze is produced from a nonwoven fabric of chemical bonded polyvinyl alcohol fiber.

\* \* \* \* \*